United States Patent [19]

Sutter et al.

[11] Patent Number: 5,093,358
[45] Date of Patent: Mar. 3, 1992

[54] MACROCYCLIC PLANT ACARICIDES

[75] Inventors: Marius Sutter, Basel; Johannes P. Pachlatko, Seltisberg, both of Switzerland; Gerhard Höfle, Braunschweig; Hans Reichenbach, Wolfenbüttel, both of Fed. Rep. of Germany

[73] Assignees: Ciba-Geigy Corp., Arsley, N.Y.; Gesellschaft fur Biotechnologische Forschung MBH, Braunschweig, Fed. Rep. of Germany

[21] Appl. No.: 563,776

[22] Filed: Aug. 7, 1990

[30] Foreign Application Priority Data

Aug. 10, 1989 [CH] Switzerland ..................... 2941/89

[51] Int. Cl.$^5$ ............................................. A01N 43/08
[52] U.S. Cl. ..................................... 514/450; 514/456
[58] Field of Search ............................. 514/450, 456

[56] References Cited

FOREIGN PATENT DOCUMENTS 282455 9/1988 European Pat. Off. .
881748 11/1988 South Africa .

OTHER PUBLICATIONS

Webster's New International Dictionary of the English Language, second edition, Springield, G. & C. Meriam Company, p. 13, 1940.

*Primary Examiner*—Allen J. Robinson
*Assistant Examiner*—John D. Pak
*Attorney, Agent, or Firm*—Kevin T. Mansfield

[57] ABSTRACT

Compounds of the formula I

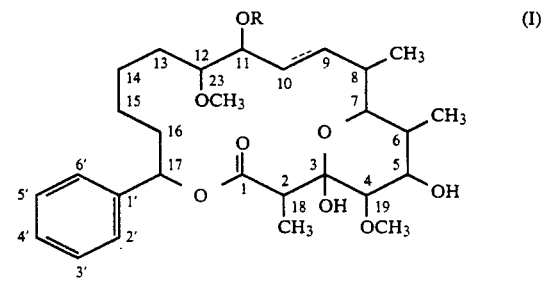

in which either R is methyl and there is a double bond in the 9,10-position, or in which R is hydrogen and there is a single bond in the 9,10-position, are highly active against Acarina which damage plants.

4 Claims, No Drawings

MACROCYCLIC PLANT ACARICIDES

The present invention relates to a method of controlling plant pests of the order of the Acarina. The acaricidal active substance used here is a compound of the formula I.

[Chemical structure of formula (I) showing a macrocyclic compound with OR, OCH3, CH3, OH substituents and a phenyl ring, with numbered positions 1-19, 23, and 1'-6']

In this formula, R is methyl if there is a double bond in the 9,10-position (=compound Ia) or R is hydrogen if there is a single bond in the 9,10-position (=compound Ib). Here and below, the name "soraphen A" will also be used for compound Ia and the name "soraphen B" for Ib. Formula I basically also comprises the isomeric structures and mixtures thereof with each other and any desired mixture of compound Ia and Ib. Soraphen A is preferred.

The macrocyclic compounds of the formula I are usually in the hemiacetal form shown, but this form can undergo a reversible ring opening reaction as shown by the equation

[Chemical equilibrium showing ring-opening reaction between hemiacetal form and open keto-hydroxy form]

Depending on the preparation and on the methods used in work-up, the compounds of the formula I are obtained in one or the other form or as a mixture of the two forms, as a function of the pH and of the solvent. A characteristic of the ring-opening reaction is the shift of the $^{13}$C-NMR signal in the 3-position and that of the $^1$H-NMR signals in certain other positions. For example, in soraphen A the following changes are observed: $^{13}$C-NMR(CDCL$_3$, δ in ppm) 99.5→203.1 (3-C). $^1$H-NMR(CDCL$_3$, δ in ppm) 3.14→3.72 (2-H); 3.18→4.5 (4-H); 3.83→3.16 (7-H); 5.86→5.7 (17-H). The formula I of the present invention basically comprises the 3-hemiacetal form which is preferred at low pH values and the open 3-keto-7-hydroxy form, as well as all possible stereoisomers which come under the formula I.

The compounds of the formula I are known from EP-A-282,455. The compounds of the formula I are obtained by microbiological culture of a Sorangium (Polyangium) cellulosum strain "So ce 26". This strain was deposited on Feb. 6, 1987, at the "National Collection of Industrial and Marine Bacteria (NCIB)", Torry Research Station, P.O. Box 31, Aberdeen, Great Britain, AB98DG under the number NCIB 12 411 in accordance with the Budapest Treaty. Sorangium cellulosum belongs to the order of the Myxobacterales, sub-order Sorangineae, family Polyangiaceae.

Surprisingly, it has now been found that the compounds of the formula I have an outstanding activity as pesticides in the control of representatives of the order Acarina and that they are therefore particularly suitable for controlling these plant pests.

The compounds of the formula I are mainly active against mites which damage plants, for example those of the families Tetranychidae, Tarsonemidae, Eriophydae, Tyroglyphidae, Panonychidae and Glycyphagidae. The compounds used according to the invention are distinguished by a good activity against all development stages of the Acarina. They act equally against adults, larvae and eggs. The compounds are mainly suitable for controlling the following mite species which attack fruit plantings, vineyards and vegetable plantings, but also cotton and ornamental plants: *Tetranychus urticae, Tetranychus cinnabarinus, Panonychus ulmi, Bryobia rubrioculus, Panonychus citri, Eriophyes pyri, Eriophyes ribis, Eriophyes vitis, Tarsonemus pallidus, Phyllocoptes vitis* and *Phyllocoptura oleivora*.

The good pesticidal action of the compounds of the formula I according to the invention corresponds to a destruction rate (mortality) of at least 50–60% of the abovementioned pests.

The action of the compounds according to the invention and of the compositions containing them can be broadened considerably and adapted to prevailing circumstances by adding other insecticides and/or acaricides. Examples of suitable additions are representatives of the following active substance classes: organic phosphorus compounds, nitrophenols and derivatives, formamidines, ureas, carbamates, pyrethroids, chlorinated hydrocarbons and avermectin B and Bacillus thuringiensis preparations. The following are typical representatives of these active substances:

Monocrotophos: dimethyl (E-1-methyl-2-methylcarbamoylvinyl)phosphate,
Carbofuran: N-methyl-2,3-dihydro-2,2-dimethylbenzofuran-7-yl carbamate,
Tetrachlorvinphos: dimethyl [Z-2-chloro-2-(2,4,5-trichlorophenyl)vinyl]phosphate,
Malathion: 5-(1,2-bisethoxycarbonylethyl)-O,O-dimethyl dithiophosphate,
Parathion-methyl: O,O-dimethyl O-(4-nitrophenyl) thiophosphate,
Carbaryl: 1-naphthyl methylcarbamate,
Methomyl: S-methyl N-methylcarbamoyloxythioacetimidate,
Chlordimeform: N'-(4-chloro-2-methylphenyl)-N,N-dimethylformamidine,
Diazinon: O,O-diethyl O-(2-isopropyl-4-methylpyrimidin-6-yl) thiophosphate,
Camphechlor: octachlorocamphene,
EPN: O-ethyl O-(4-nitrophenyl) phenylthiophosphonate,
Deltamethrin: (S)-α-cyano-3-phenoxybenzyl (1R,3R)-3-(2,2-dibromovinyl)-2,2-dimethylcyclopropanecarboxylate,
Oxamyl: N,N-dimethyl-α-methylcarbamoyloxyimino-α-methylthio-acetamide,
Fenvalerate: (RS)-α-cyano-3-phenoxybenzyl (RS)-2-(4-chlorophenyl)-3-methylbutyrate,
Permethrin: 3-phenoxybenzyl (1RS,3RS; 1RS,3SR)-3-(2,2-dichlorovinyl)-2,2-dimethylcyclopropanecarboxylate,
Cypermethrin: (RS)-α-cyano-3-phenoxybenzyl (1RS,3RS; 1RS,3SR)-3-(2,2-dichlorovinyl)-2,2-dimethylcyclopropanecarboxylate, Profenofos: O-ethyl O-(4-bromo-2-chlorophenyl) S-propyl thiophosphate, Sulfprofos: O-ethyl O-(4-methylthiophenyl) S-propyl dithiophosphate, Triflumuron: N-(4-trifluoromethoxyphenyl)-N'-(2-chlorobenzoyl)urea, Diflubenzuron: N-(4-chlorophenyl)-N'-(2,6-difluorobenzoyl)urea, Methoprene: isopropyl (E,E)-(RS)-11-methoxy-3,7,11-trimethyldodeca-2,4-dienoate, Buprofezine: 2-tert-butylimino-3-isopropyl-5-phenyl-1,3,5-thiadiazinan-4-one, Thiodicarb: 3,7,9,13-tetramethyl-5,11,dioxa-2,8,14-trithia-4,7,9,12-tetraazapentadeca-3,12-diene-6,10-dione, Acephate: N-[methoxy-(methylthio)-phosphinoyl]-acetamide, Azinphos-methyl: S-(2,5-dihydro-4-oxo-1,2,3-benzotriazin-3-ylmethyl) O,O-dimethyl dithiophosphate, Chlorpyrifos: O,O-diethyl O-(3,5,6-trichloropyrid-2-yl) thiophosphate, Dimethoate: O,O-dimethyl S-methylcarbamoylmethyl dithiophosphate, Fonophos: O-ethyl S-phenyl (RS)-ethanedithiophosphonate, Isofenphos: isopropyl O-[ethoxy-(isopropylamino)-phosphinothioyl]salicylate, Methidathion: S-2,3-dihydro-5-methoxy-2-oxo-1,3,4-thiadiazol-3-ylmethyl O,O-dimethyl dithiophosphate, Methamidiphos: O,S-dimethyl phosphoramidothioate, Monocrotophos: (E)-(1-methyl-2-methylcarbamoyl-vinyl)-dimethyl phosphate, Phosmet: O,O-dimethyl S-phthalimidomethyl dithiophosphate, Phosphamidon: 2-chloro-2-diethylcarbamoyl-1-methyl-vinyl dimethyl phosphate, Phosalone: O,O-diethyl S-(6-chloro-2,3-dihydro-2-oxo-1,3-benzoxazol-3-ylmethyl) dithiophosphate, Pirimicarb: O-(2-dimethylamino-5,6-dimethylpyrimidin-4-yl) dimethylcarbamate, Phorate: S-ethylthiomethyl O,O-diethyl dithiophosphate, Terbufos: S-tert-butylthiomethyl O,O-diethyl dithiophosphate, Trichlorfon: O,O-dimethyl 2,2,2-trichloro-1-hydroxyethylphosphonate, Methoxychlor: 1,1,1-trichloro-2,2-bis(4-methoxyphenyl)ethane, Bifenthrin: 2-methyl-3-phenylbenzyl (Z)-(1RS,3RS)-3-(2-chloro-3,3,3-trifluoroprop-1-enyl)-2,2-dimethylcyclopropanecarboxylate, Cyfluthrin: (RS)-α-cyano-4-fluoro-3-phenoxybenzyl (1RS,3RS; 1RS,3SR)-3-(2,2-dichlorovinyl)-2,2-dimethylcyclopropanecarboxylate, Fenpropathrin: (RS)-α-cyano-3-phenoxybenzyl 2,2,3,3-tetramethylcyclopropanecarboxylate, Fluvalinate: (RS)-α-cyano-3-phenoxybenzyl N-(2-chloro-4-trifluoromethylphenyl)valinate, Flucythrinate: (RS)-α-cyano-3-phenoxybenzyl (S)-2-(4-difluoromethoxyphenyl)-2-methylbutyrate, Tralomethrin: (S)-α-cyano-3-phenoxybenzyl (1RS,3S)-2,2-dimethyl-3-[(RS)-1,2,2,2-tetrabromoethyl]-cyclopropanecarboxylate, Bifenate: 2-methyl-3-phenyl-benzyl (Z)-(1RS,3RS)-3-(2-chloro-3,3,3-trifluoroprop-1-enyl)-2,2-dimethylcyclopropanecarboxylate, Metaldehyde: 2,4,6,8-tetramethyl-1,3,5,7-tetraoxocyclooctane, Rotenone: (2R,6aS,12aS)-1,2,6,6a,12,12a-hexahydro-2-isopropenyl-8,9-dimthoxychromeno[3,4-b]furo[2,3-h]chromen-6-one, Binapacryl: 2-sec.butyl-4,6-dinitrophenyl 3-methylcrotonate, Quinomethionate: 6-methyl-1,3-dithiolo[4,5-]quinoxalin-2-one, Chlorobenzilate: ethyl 4,4'-dichlorobenzilate, Dicofol: 2,2,2-trichloro-1,1-bis(4-chlorophenyl)ethanol, Dienochlor: perchloro-1,1'-bicyclopenta-2,4-diene, Bisclofentezin: 3,6-bis(2-chlorophenyl)-1,2,4,5-tetrazine, Cyhexatin: tricyclohexylhydroxystannane, Hexythiazox: N-cyclohexyl-(4RS,5RS)-5-(4-chlorophenyl)-4-methyl-2-oxo-1,3-thiazolidine-3-carboxamide, Amitraz: N,N-bis(2,4-xylyliminomethyl)methylamine, Propargite: 2-(4-tert.butylphenoxy)-cyclohexyl-propargyl sulfite, Fenbutatin-oxide: hexakis-(2-methyl-2-phenylpropyl)-distannanoxane.

The compounds of the formula I are employed in unaltered form, i.e., as a pure crystalline substance or as the biomass obtained from the fermentation, dried and ground, or, preferably, together with the auxiliaries conventionally used in the art of formulation, and they can therefore be processed in a known manner for example to emulsion concentrates, directly sprayable or dilutable solutions, dilute emulsions, wettable powders, soluble powders, dusts, granules and also encapsulations in polymeric substances. The application methods, such as spraying, misting, atomizing, scattering or pouring, as well as the compositions, are selected to suit the intended aims and the prevailing circumstances.

The formulations, i.e. the compositions, preparations or combinations, containing the active substance of the formula I or combinations of these active substances with other insecticides or acaricides, and, if desired, a solid or liquid additive, are prepared in a known manner, for example by intimately mixing and/or grinding the active substances with extenders, for example with solvents, solid carriers, and, if desired, surface-active compounds (surfactants).

The following are possible as solvents: aromatic hydrocarbons, preferably the fractions $C_8$ to $C_{12}$, for example xylene mixtures or substituted naphthalenes, phthalic esters, such as dibutyl phthalate or dioctyl phthalate, aliphatic hydrocarbons, such as cyclohexane, paraffins, alcohols and glycols as well as their ethers and esters, such as ethanol, ethylene glycol, ethylene glycol monomethyl ether or ethylene glycol monoethyl ether, ketones, such as cyclohexanone, strongly polar solvents, such as N-methyl-2-pyrrolidone, dimethyl sulfoxide or dimethylformamide, and also epoxidized or unepoxidized vegetable oils, such as epoxidized coconut oil or soya oil, or water.

Solid carriers which are generally used, for example for dusts and dispersible powders, are ground natural minerals, such as calcite, talc, kaolin, montmorillonite or attapulgite. To improve the physical properties, it is also possible to add highly-disperse silicas or highly-disperse absorptive polymers.

Possible particulate, adsorptive carriers for granules are either porous types, for example pumice, brick grit, sepiolite or bentonite, and also non-sorptive carrier materials, such as calcite or sand. Moreover, a large number of granulated materials of inorganic or organic nature can be used, such as, in particular, dolomite or comminuted plant residues.

Suitable surface-active compounds are non-ionic, cationic and/or anionic surfactants having good emulsifying, dispersing and wetting properties, depending on the nature of the active substance of the formula I to be formulated or on the combination of these active substances with other insecticides or acaricides. Surfactants are also to be understood as meaning mixtures of surfactants.

Anionic surfactants which are suitable can be either so-called water-soluble soaps or water-soluble synthetic surface-active compounds.

Suitable soaps are the alkali metal salts, alkaline earth metal salts or substituted or unsubstituted ammonium salts of higher fatty acids ($C_{10}$–$C_{22}$), such as the sodium salts or potassium salts of oleic or stearic acid, or of natural mixtures of fatty acids which can be obtained, for example, from coconut or tall oil. Mention must also be made of the fatty acid methyltaurinates and modified and unmodified phospholipids.

However, so-called synthetic surfactants are used more frequently, in particular fatty sulfonates, fatty sulfates, sulfonated benzimidazole derivatives or alkylarylsulfonates.

The fatty sulfonates or fatty sulfates are generally in the form of alkali metal salts, alkaline earth metal salts or substituted or unsubstituted ammonium salts, and generally have an alkyl radical having 8 to 22 C atoms, alkyl also including the alkyl moiety of acyl radicals, for example the sodium or calcium salt of lignosulfonic acid, of the dodecylsulfuric ester or of a fatty alcohol sulfate mixture prepared from natural fatty acids. This group also includes the salts of the sulfuric esters and sulfonic acids of fatty alcohol/ethylene oxide adducts. The sulfonated benzimidazole derivatives preferably contain 2 sulfonyl groups and one fatty acid radical having about 8-22 C atoms. Examples of alkylarylsulfonates are the Na, Ca or triethanolamine salts of dodecylbenzenesulfonic acid, of dibutylnaphthalenesulfonic acid or of a naphthalenesulfonic acid/formaldehyde condensation product. Other suitable compounds are the corresponding phosphates, such as the salts of the phosphoric ester of a p-nonylphenol/(4-14)-ethylene oxide adduct.

Suitable non-ionic surfactants are mainly polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl radical of the alkylphenols. Other non-ionic surfactants which are suitable are the water-soluble polyethylene oxide adducts with polypropylene glycol, ethylenediaminopolypropylene glycol and alkylpolypropylene glycol which have 1 to 10 carbon atoms in the alkyl chain and which contain 20 to 250 ethylene glycol ether groups and 10 to 100 propylene glycol ether groups. The abovementioned compounds customarily contain 1 to 5 ethylene glycol units per propylene glycol unit.

Examples of non-ionic surfactants which may be mentioned are nonylphenolpolyethoxyethanols, castor oil polyglycol ethers, castor oil thioxilate, polypropylene/polyethylene oxide adducts, tributylphenoxypolyethoxyethanol, polyethylene glycol and octylphenoxypolyethoxyethanol. Other suitable substances are fatty acid esters of polyoxyethylenesorbitan, such as polyoxyethylenesorbitan trioleate.

The cationic surfactants are mainly quaternary ammonium salts which contain at least one alkyl radical having 8 to 22 C atoms as N-substituent and which have lower halogenated or free alkyl, benzyl or lower hydroxyalkyl radicals as further substituents. The salts are preferably in the form of halides, methylsulfates or ethylsulfates, for example stearyltrimethylammonium chloride or benzyldi(2-chloroethyl)ethylammonium bromide.

The surfactants customary in the art of formulation are described, inter alia, in the following publications:

"1985 International McCutcheon's Emulsifiers & Detergents", Glen Rock, N.J., U.S.A., 1985", H. Stache, "Tensid-Taschenbuch [Surfactant Guide]", 2nd edition, C. Hanser Verlag Munich, Vienna 1981, M. and J. Ash. "Encyclopedia of Surfactants", Vol. I-III, Chemical Publishing Co., New York, 1980-1981.

As a rule, the pesticidal preparations contain 0.1 to 99%, in particular 0.1 to 95%, of the active substance of the formula I or combinations of this active substance with other insecticides or acaricides, 1 to 99.9% of a solid or liquid additive and 0 to 25%, in particular 0.1 to 20%, of a surfactant. While concentrated compositions are often preferred as commercially available goods, the end user generally uses dilute preparations containing considerably lower concentrations of active substance. Typical application concentrations are between 0.1 and 1,000 ppm, preferably between 0.1 and 500 ppm. The application rates per hectare are generally 1 to 1,000 g of active substance per hectare, preferably 1 to 100 g/ha.

In particular, preferred formulations have the following composition: (%=per cent by weight)

| Emulsifiable concentrates | | |
|---|---|---|
| Active ingredient: | 1 to 20%, | 5 to 10% being preferred |
| Surface-active agent: | 5 to 30%, | preferably 10 to 20% |
| Liquid carrier: | 50 to 94%, | preferably 70 to 85% |
| Dusts: | | |
| Active ingredient: | 0.1 to 10%, | preferably 0.1 to 1% |
| Solid carrier: | 99.9 to 90%, | preferably 99.9 to 99% |
| Suspension concentrates: | | |
| Active ingredient: | 5 to 75%, | preferably 10 to 50% |
| Water: | 94 to 24%, | preferably 88 to 30% |
| Surface-active agent: | 1 to 40%, | preferably 2 to 30% |
| Wettable powders: | | |
| Active ingredient: | 0.5 to 90%, | preferably 1 to 80% |
| Surface-active agent: | 0.5 to 20%, | preferably 1 to 15% |
| Solid carrier material: | 5 to 95%, | preferably 15 to 90% |
| Granules: | | |
| Active ingredient: | 0.5 to 30%, | preferably 3 to 15% |
| Solid carrier: | 99.5 to 70%, | preferably 97 to 85% |

The compositions can also contain further additions, such as stabilizers, defoamers, preservatives, viscosity regulators, binders, tackifiers and also fertilizers or other active substances for achieving specific effects.

The examples which follow are intended to illustrate the invention. They do not restrict the invention.

FORMULATION EXAMPLES OF THE ACTIVE SUBSTANCE OF THE FORMULA I
(%=PERCENT BY WEIGHT)

| 1. Emulsion concentrates | (a) | (b) | (c) |
|---|---|---|---|
| Active substance Ia or Ib | 25% | 40% | 50% |
| Ca dodecylbenzenesulfonate | 5% | 8% | 6% |
| Castor oil polyethylene glycol ether (36 mol of ethylene oxide) | 5% | — | — |
| Tributylphenol polyethylene glycol ether (30 mol of ethylene oxide) | — | 12% | 4% |
| Cyclohexanone | — | 15% | 20% |
| Xylene mixture | 65% | 25% | 20% |

Emulsions of any desired concentration can be prepared from such concentrates by dilution with water.

| 2. Solutions | (a) | (b) | (c) | (d) |
|---|---|---|---|---|
| Active substance Ia or Ib | 80% | 10% | 5% | 95% |
| Ethylene glycol monomethyl ether | 20% | — | — | — |
| Polyethylene glycol MW 400 | — | 70% | — | — |
| N-Methyl-2-pyrrolidone | — | 20% | — | — |
| Epoxidized coconut oil | — | — | 1% | 5% |
| Petroleum ether (boiling range 160–190° C.) | — | — | 94% | — |

(MW = molecular weight)

The solutions are suitable for application in form of minute droplets.

| 3. Granules | (a) | (b) |
|---|---|---|
| Active substance Ia or Ib | 5% | 10% |
| Kaolin | 94% | — |
| Highly-disperse silica | 1% | — |
| Attapulgite | — | 90% |

The active substance is dissolved in methylene chloride, the solution is sprayed onto the carrier, and the solvent is subsequently evaporated in vacuo.

| 4. Dusts | (a) | (b) |
|---|---|---|
| Active substance Ia or Ib | 2% | 5% |
| Highly-disperse silica | 1% | 5% |
| Talc | 97% | — |
| Kaolin | — | 90% |

Ready-to-use dusts are obtained by intimately mixing the carrier substances with the active substance. These dusts can then be ground by adding more of the three carrier substances to give ready-to-use dusts with 0.001% of active substance.

| 5. Wettable powders | (a) | (b) | (c) |
|---|---|---|---|
| Active substance Ia or Ib | 25% | 50% | 75% |
| Na liginsulfonate | 5% | 5% | — |
| Na lauryl sulfate | 3% | — | 5% |
| Na diisobutylnaphthalenesulfonate | — | 6% | 10% |
| Octylphenol polyethylene glycol ether (7-8 mol of ethylene oxide) | — | 2% | — |
| Highly-disperse silica | 5% | 10% | 10% |
| Kaolin | 62% | 27% | — |

The active substance is mixed thoroughly with the additives and the mixture is ground thoroughly in a suitable mill. This gives wettable powders which can be diluted with water to give suspensions of any desired concentration.

| 6. Coated granules | |
|---|---|
| Active substance Ia or Ib | 3% |
| Polyethylene glycol (MW 200) | 3% |
| Kaolin | 94% |

(MW = molecular weight)

In a mixer, the finely ground active substance is applied uniformly to the kaolin which has been moistened with the polyethylene glycol. In this manner, dust-free coated granules are obtained.

| 7. Suspension concentrate | |
|---|---|
| Active substance Ia or Ib | 40% |
| Ethylene glycol | 10% |
| Nonylphenyl polyethylene glycol ether 15 mol of ethylene oxide) | 6% |
| Na ligninsulfonate | 10% |
| Carboxymethylcellulose | 1% |
| 37% aqueous formaldehyde solution | 0.2% |
| Silicone oil in form of a 75% aqueous emulsion | 0.8% |
| Water | 32% |

The finely ground active substance is mixed intimately with the additives. This gives a suspension concentrate from which suspensions of any desired concentration can be prepared by dilution with water.

8. Biomass concentrate

The biomass obtained from the production culture is dried, ground and mixed with ethylene glycol monomethyl ether in a ratio by weight of 80:20. Such a concentrate can be diluted with water as desired to give spray suspensions.

BIOLOGICAL EXAMPLES

EXAMPLE 1: Action against *Tetranychus urticae*

Young bean plants are infested with a mixed population of *Tetranychus urticae* and, 1 day later, sprayed with an aqueous emulsion spray liquor which contains 400 or 200 ppm of the active substance. The plants are subsequently incubated for 6 days at 25° C. and then evaluated. The percentage reduction of the population (% action) is determined by comparing the number of dead eggs, larvae and adults on treated plants with that of the untreated plants.

At 400 and 200 ppm, the compounds Ia and Ib show a 100% action against adults, larvae and eggs of *Tetranychus urticae* in this test.

EXAMPLE 2: Action against *Panonychus ulmi* (OP- and carb.-resistant)

Apple seedlings are infested with adult female *Panonychus ulmi*. After seven days, the infected plants are sprayed to run-off point with an aqueous emulsion spray liquor containing 100 or 50 ppm of a compound to be tested, and grown in the greenhouse. The evaluation takes place after 14 days. The percentage reduction of the population (% action) is determined by comparing the number of dead mites on the treated plants with that of the untreated plants.

At 100 and at 50 ppm, the compounds Ia and Ib show a 100% action against adults, larvae and eggs of *Panonychus ulmi* in this test.

EXAMPLE 3: Action against *Tetranychus cinnabarinus*

Young bean plants are infested with a mixed population of *Tetranychus cinnabarinus* and, 1 day later, sprayed with an aqueous emulsion spray liquor which contains 200 ppm of the active substance. The plants are subsequently incubated for 9 days at 25° C. and then evaluated. The percentage reduction of the population (% action) is determined by comparing the number of dead eggs, larvae and adults on treated plants with that of the untreated plants.

The compounds Ia and Ib show a 100% action against adults and larvae of *Tetranychus cinnabarinus* in this test. An action of more than 90% is achieved against eggs.

We claim:

1. A method of controlling phytopathogenic Acarina, which comprises treating Acarina-infested plants or the Acarina-infested habitat of said Acarina with an effective amount of an active substance of the formula I

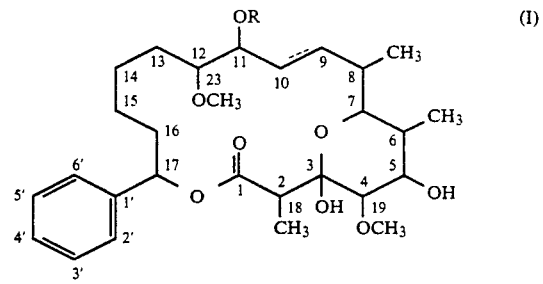

in which either R is methyl and there is a double bond in the 9,10-position, or in which R is hydrogen and there is a single bond in the 9,10-position.

2. A method according to claim 1, wherein the active substance is the compound of the formula Ia

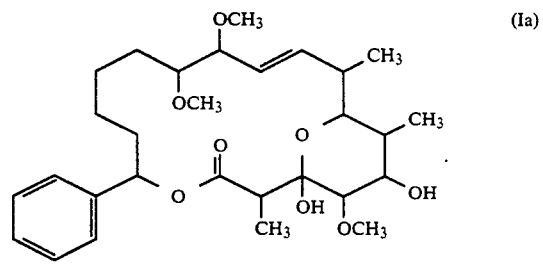

3. A method according to claim 1 for controlling the mite families Tetranychidae and Panonychidae.

4. A method according to claim 1 for controlling *Tetranychus urticae*, *Tetranychus cinnabarinus* and *Panonychus ulmi*.

* * * * *